US012631614B2

(12) United States Patent
Liao et al.

(10) Patent No.: US 12,631,614 B2
(45) Date of Patent: May 19, 2026

(54) METHOD FOR TRACING SEDIMENT SOURCE BASED ON SIZE DISTRIBUTION AND CORRESPONDING MASS PERCENTAGES

(71) Applicant: Shanghai Investigation, Design & Research Institute Co., Ltd., Shanghai (CN)

(72) Inventors: Tingting Liao, Shanghai (CN); Songliu Lu, Shanghai (CN); Lin Lin, Shanghai (CN); Xiaotao Wu, Shanghai (CN); Zhiyan Yang, Shanghai (CN); Huating Xu, Shanghai (CN); Lin Liu, Shanghai (CN)

(73) Assignee: Shanghai Investigation, Design & Research Institute Co., Ltd., Shanghai (CN)

( * ) Notice: Subject to any disclaimer, the term of this patent is extended or adjusted under 35 U.S.C. 154(b) by 0 days.

(21) Appl. No.: 18/574,318

(22) PCT Filed: Apr. 21, 2023

(86) PCT No.: PCT/CN2023/089879
§ 371 (c)(1),
(2) Date: Oct. 31, 2024

(87) PCT Pub. No.: WO2024/207560
PCT Pub. Date: Oct. 10, 2024

(65) Prior Publication Data
US 2026/0016457 A1     Jan. 15, 2026

(30) Foreign Application Priority Data
Apr. 4, 2023     (CN) .......................... 202310352983.4

(51) Int. Cl.
*G01N 3/24*          (2006.01)
*G01N 15/02*         (2024.01)
*G01N 33/24*         (2006.01)
(52) U.S. Cl.
CPC ............. *G01N 33/24* (2013.01); *G01N 15/02* (2013.01); *G01N 2015/0288* (2013.01)
(58) Field of Classification Search
CPC . G01N 15/02; G01N 2015/0288; G01N 33/24
See application file for complete search history.

(56) References Cited

FOREIGN PATENT DOCUMENTS

| | | |
|---|---|---|
| CN | 110033133 A | 7/2019 |
| CN | 113536598 A | 10/2021 |
| KR | 20180000619 A | 1/2018 |

OTHER PUBLICATIONS

Aksakal et al, A new approach for calculating aggregate stability: Mean weight aggregate stability (MWAS), Catena 194 (2020) 104708 (Year: 2020).*
Upadhayay et al, Sensitivity of source apportionment predicted by a Bayesian tracer mixing model to the inclusion of a sediment connectivity index as an informative prior: Illustration using the Kharka catchment (Nepal), Science of the Total Environment 713 (2020) 136703, Elsevier (Year: 2020).*
Lewis et al, Determination of Suspended Sediment Concentrations and Particle Size Distributions Using Pressure Measurements, J. Environ. Qual. 28:1490-1496 (1999) (Year: 1999).*
Guo, Jin et al.,Quantifying Catchment Scale Sediment Source Using Composite Fingerprinting Technique), Transactions of The Chinese Society of Agricultural Engineering, vol. {0} 30, No. {0} 2, Jan. 31, 2014 (Jan. 31, 2014), pp. 94-104, ISSN: 1002-6819, CN.
Du, Pengfei et al., "Using Source Fingerprinting Techniques to Investigate Sediment Sources during Snowmelt and Rainfall Erosion Events in a Small Catchment in the Black Soil Region of Northeast China", land,Feb. 23, 2023 (Feb. 23, 2023), pp. 1-20, Switzerland.
Cao, Wenhong, Review of Research Progress in Application of Fingerprinting Method to Determination of Sediment Source), Journal of China Institute of Water Resources and Hydropower Research,vol. {0} 16, No. {0} 5, Oct. 31, 2018 (Oct. 31, 2018), pp. 353-361,ISSN:2097-096X, CN.

* cited by examiner

*Primary Examiner* — David L Singer
(74) *Attorney, Agent, or Firm* — The Inventor's Friend Patent Law Firm, P.L.L.C.; Nathaniel A. Wickliffe

(57)          ABSTRACT
The method for tracing a sediment source, including: sampling at sampling points and multiple additional testing points around each sampling point; measuring sediment grain size distribution and corresponding mass percentages to plot sediment grain size distribution curves of each sampling point and its additional testing points; plotting a sediment fingerprint matrix of each sampling point; comparing patterns of the sediment fingerprint matrix of the first sampling point with patterns of the sediment fingerprint matrix of the second sampling point, and determining whether sediment at the first sampling point and that at the second sampling point have the same source. The sediment fingerprint matrix that illustrates the variation of sediment characteristics in different grain size intervals. In addition, by comparing the sediment characteristics in the corresponding grain size intervals, the tracing and classification of sediment from different locations can be achieved.

4 Claims, 2 Drawing Sheets

METHOD FOR TRACING SEDIMENT SOURCE BASED ON SIZE DISTRIBUTION AND CORRESPONDING MASS PERCENTAGES

FIELD OF THE INVENTION

The present disclosure relates to the technical field of soil erosion prevention and channel sedimentation and erosion protection, in particular to a method for tracing a sediment source.

BACKGROUND OF THE INVENTION

Soil erosion induced by rainfall runoff is the main driving factor for the loss of surface soil and nutrients, which can lead to soil degradation and threaten the sustainable development of agriculture. It also results in a large amount of sediment and related nutrients entering rivers and lakes, causing deterioration of water bodies and the ecological environment. Accurately identifying the source of sediment and calculating the sediment load of rivers is a prerequisite for effectively preventing and controlling sediment from entering rivers and lakes.

Existing sediment tracing methods include observation-based methods and erosion monitoring methods. However, these tracing methods are heavily influenced by human factors, making it difficult to ensure the completeness of the collected information and observed data in terms of time and space. At the same time, these tracing methods lack an accurate understanding of the true source of sediment and the changes in source-sink relationships caused by migration processes. As a result, the identification and classification of sediment source areas cannot fully and effectively reflect the sediment source-sink processes.

Therefore, how to improve the accuracy of source identification and classification when tracing sediment becomes a pressing technical issue for professionals in this field.

SUMMARY OF THE INVENTION

The present disclosure provides a method for tracing a sediment source.

The method for tracing the sediment source includes:

S100: sampling at sampling points and multiple additional testing points around each sampling point;

where the sampling points include a first sampling point and a second sampling point;

S200: measuring sediment grain size distribution and corresponding mass percentages to plot sediment grain size distribution curves of each sampling point and its additional testing points;

S300: plotting a sediment fingerprint matrix of each sampling point;

where a horizontal axis of the sediment fingerprint matrix represents grain size, a vertical axis of the sediment fingerprint matrix represents mass percentage, and elements of the sediment fingerprint matrix are the number of the sediment grain size distribution curves;

S400: comparing patterns of the sediment fingerprint matrix of the first sampling point with patterns of the sediment fingerprint matrix of the second sampling point, and determining whether sediment at the first sampling point and that at the second sampling point have the same source, where the patterns refer to columns of the sediment fingerprint matrix of each sampling point.

In an embodiment, the ratio of the number of the sampling points to the number of additional testing points of each sampling point is 1:4, and the four additional testing points are evenly distributed around each sampling point in a circular pattern.

In an embodiment, the four additional testing points are respectively located upstream, downstream, and on the left and right sides of each sampling point.

In an embodiment, a distance between each additional testing point and its corresponding sampling point is in a range of 50 cm to 100 cm.

The present disclosure has the following beneficial effects:

by sampling the sediment at the sampling points and additional testing points around them and using the grain size distribution curves of sediment at the sampling points and additional testing points, the present disclosure provides the sediment fingerprint matrix that illustrates the variation of sediment characteristics in different grain size intervals. In addition, by comparing the sediment characteristics in the corresponding grain size intervals, the precise tracing and classification of sediment from different locations can be achieved.

DETAILED DESCRIPTION OF THE INVENTION

Specific embodiments of the present disclosure are described in further detail below in conjunction with the accompanying drawings. These embodiments are only used to illustrate the present disclosure and are not intended to limit the present disclosure.

In the description of the present disclosure, it should be noted that the terms "center", "longitudinal", "transverse", "up", "down", "front", "back", "left", "right", "vertical", "horizontal", "top", "bottom", "inside", "outside", and other indications of direction or positional relationships are based on the orientation or positional relationships shown in the accompanying drawings. They are only used for the convenience of describing the present disclosure and simplifying the description, and do not indicate or imply that the device or component referred to must have a specific orientation, be constructed or operated in a specific orientation. Therefore, they should not be construed as a limitation of the present disclosure. Furthermore, the terms "first" and "second" are used for descriptive purposes only and should not be understood as indicating or implying relative importance.

In the description of the present disclosure, it should be noted that unless otherwise specified and limited, the terms "mounted", "connected", and "communicated" should be broadly interpreted. For example, they may be a fixed connection or a detachable connection, or a connection in one piece; they may be a mechanical connection or an electrical connection; they may be a direct connection or an indirect connection through an intermediate medium; or they may be a communication within two components. For those of ordinary skill in the art, the specific meanings of the above terms in the present disclosure may be understood case by case.

In addition, in the description of the present disclosure, unless otherwise specified, the term "multiple" means two or more.

EMBODIMENT

Figure 1:
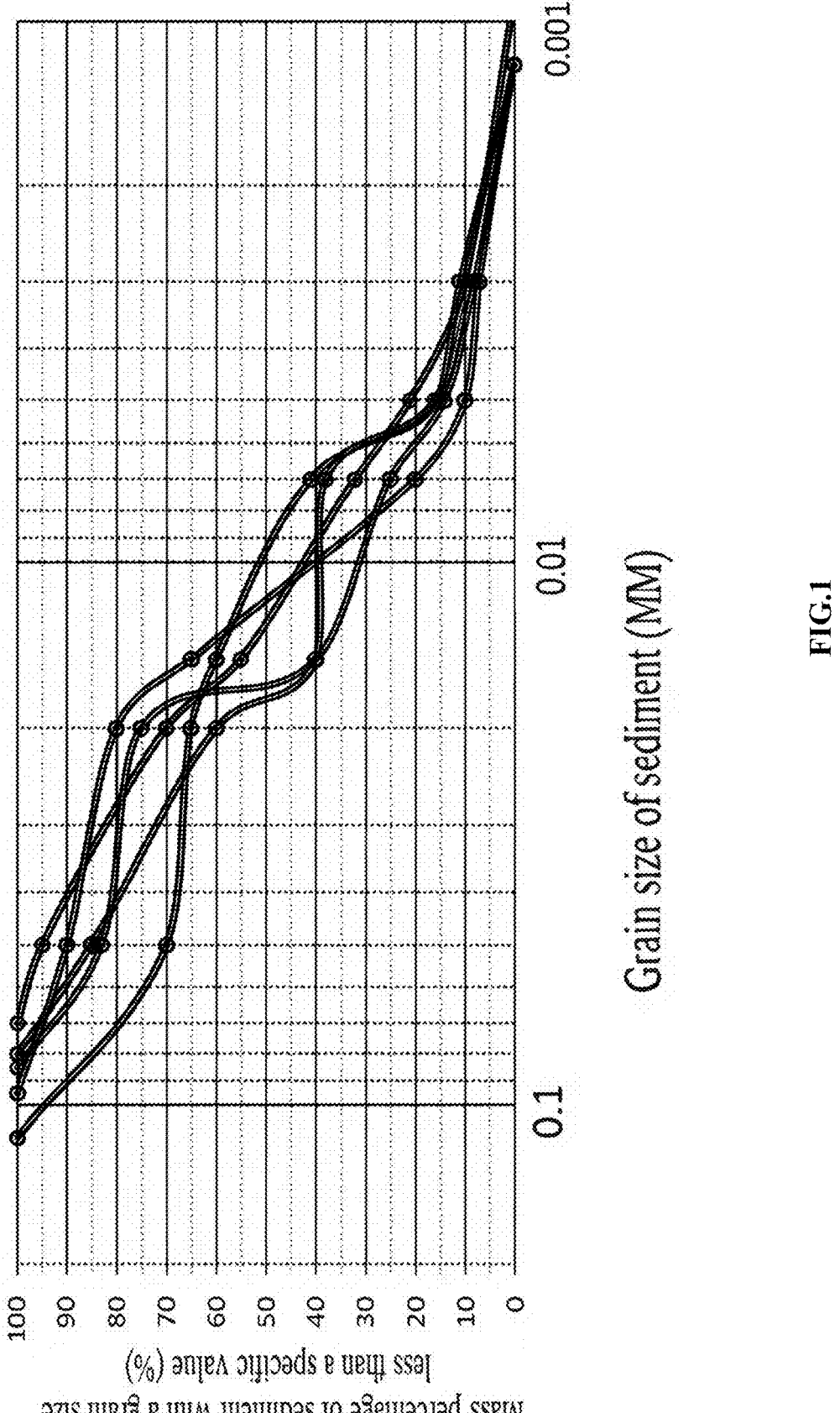
FIG. 1 shows grain size distribution curves of a first sampling point and its additional testing points.
Figure 2:
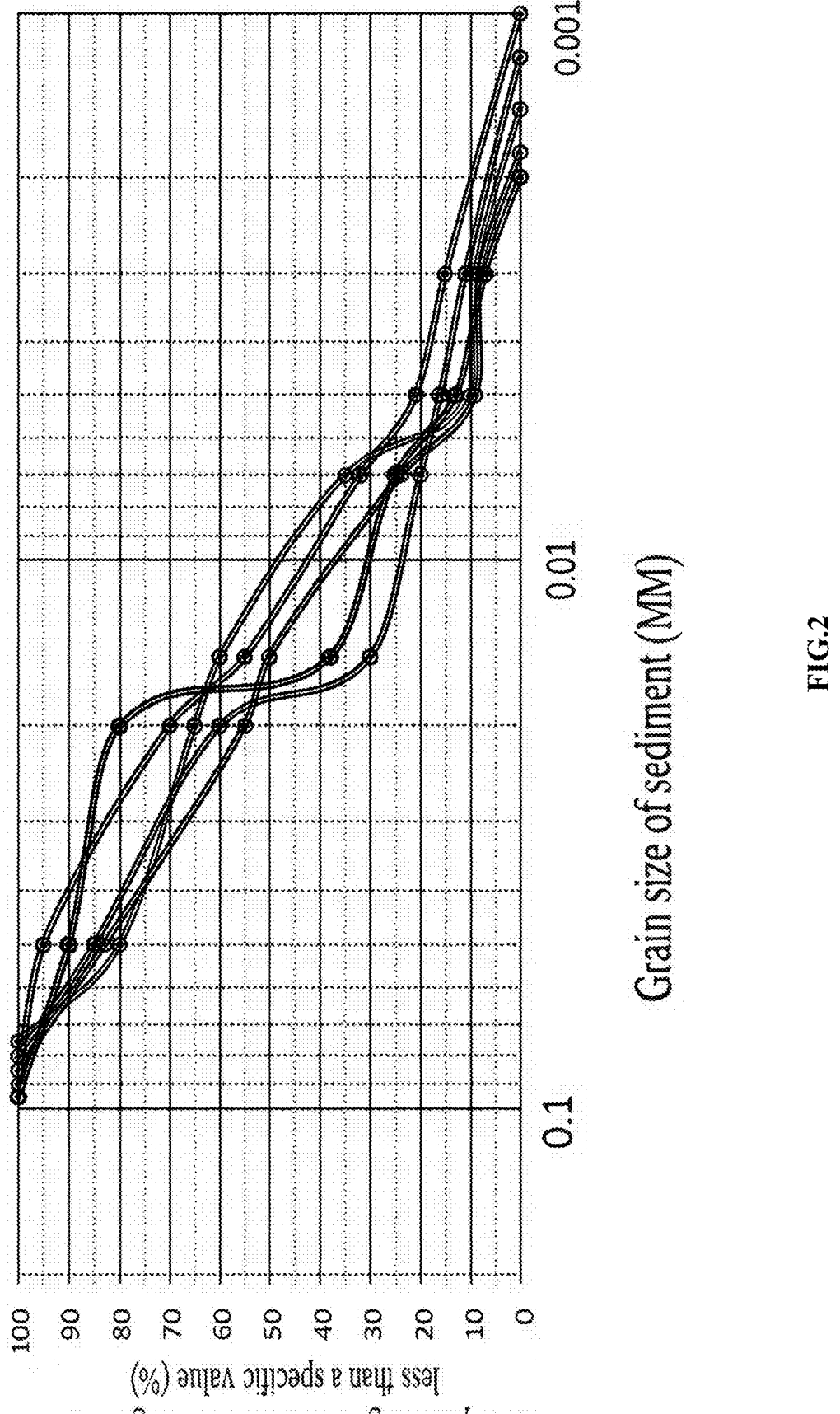
FIG. 2 shows grain size distribution curves of a second sampling point and its additional testing points.

As shown in FIGS. 1 and 2, a method for tracing a sediment source is provided, including:

S100: sampling at sampling points and multiple additional testing points around each sampling point to obtain multiple sediment samples.

The sampling points include a first sampling point and a second sampling point, that is, the number of the sampling points is two or more.

S200: Measuring the sediment grain size distribution and the corresponding mass percentage of different grain sizes for each sediment sample, plotting sediment grain size distribution curves for the sediment samples collected from sampling points and their additional testing points.

S300: Setting multiple grain size intervals based on the sediment grain size distribution curves of the sampling points and the additional testing points, and plotting a sediment fingerprint matrix of the sampling points and the additional testing points according to the grain size intervals and the corresponding mass percentages for the grain size intervals.

The horizontal axis of the sediment fingerprint matrix represents grain size, the vertical axis represents mass percentage, and the elements of the sediment fingerprint matrix are the number of sediment grain size distribution curves.

S400: Comparing the patterns of the first sampling point and the second sampling point, and determining whether the sediment at the first sampling point and that at the second sampling point have the same source.

The patterns refer to the columns of the sediment fingerprint matrix of each sampling point.

By sampling the sediment at the sampling points and additional testing points around them and using the grain size distribution curves of sediment at the sampling points and additional testing points, the present disclosure provides a sediment fingerprint matrix that illustrates information on the variation of sediment characteristics in different grain size intervals. In addition, by comparing the sediment characteristics in the corresponding grain size intervals, the precise tracing and classification of sediment from different locations can be achieved.

In an embodiment, the ratio of the number of the sampling points to the number of additional testing points of each sampling point is 1:4, and the four additional testing points are evenly distributed around each sampling point in a circular pattern.

In an embodiment, the four additional testing points are located upstream, downstream, and on the right and left sides of the sampling point.

In an embodiment, the distance between each additional testing point and its corresponding sampling point is in a range of 50 cm to 100 cm.

In a specific embodiment, the method for tracing the sediment source includes:

S100: sampling at sampling point A and its four additional testing points and sampling at sampling point B and its four additional testing points to obtain a total of ten sediment samples, where the sampling point A is located upstream the sampling point B, the four additional testing points of the sampling point A are respectively located on a top side, bottom side, left side, and right side of the sampling point A and each one is located 1000 mm away from the sampling point A, and the four additional testing points of the sampling point B are respectively located on a top side, bottom side, left side, and right side of the sampling point B and each one is located 1000 mm away from the sampling point B.

S200: Measuring the sediment grain size distribution and the corresponding mass percentage of different grain sizes for each of the ten sediment samples, and plotting the sediment grain size distribution curve for the ten sediment samples collected from the sampling point A, the sampling point B, and the eight additional testing points.

S300: Setting multiple grain size intervals based on the sediment grain size distribution curve of the sampling points and the additional testing points, and plotting the sediment fingerprint matrices of the sampling points and the additional testing points according to the grain size intervals and the corresponding mass percentages for the grain size intervals. For example, the grain size intervals can be 0.1 mm, 0.05 mm, 0.02 mm, 0.015 mm, 0.007 mm, 0.005 mm, 0.003 mm, and 0.001 mm. The division of mass percentages is: (0%, 10%], (10%, 25%], (25%, 40%], (40%, 55%], (55%, 70%], (70%, 85%], and (85%, 100%].

The horizontal axis of the sediment fingerprint matrix represents grain size, the vertical axis represents mass percentage, and the elements of the sediment fingerprint matrix are the number of sediment grain size distribution curves.

For example, Table 1 shows various grain size intervals on five sediment grain size distribution curves of the sampling point A and its four additional testing points as well as the corresponding mass percentages.

TABLE 1

| Grain size distribution curve 1 | | Grain size distribution curve 2 | | Grain size distribution curve 3 | | Grain size distribution curve 4 | | Grain size distribution curve 5 | |
|---|---|---|---|---|---|---|---|---|---|
| Grain size | Percentage | Grain size | Percentage | Grain size | Percentage | Grain size | Percentage | Grain size | Percentage |
| 0.07 | 100 | 0.08 | 100 | 0.115 | 100 | 0.085 | 100 | 0.095 | 100 |
| 0.05 | 95 | 0.05 | 85 | 0.05 | 70 | 0.005 | 83 | 0.005 | 90 |
| 0.02 | 70 | 0.02 | 60 | 0.02 | 65 | 0.02 | 75 | 0.002 | 80 |
| 0.015 | 55 | 0.015 | 40 | 0.015 | 60 | 0.015 | 40 | 0.015 | 65 |
| 0.007 | 32 | 0.007 | 38 | 0.007 | 41 | 0.007 | 25 | 0.007 | 20 |
| 0.005 | 21 | 0.005 | 16 | 0.005 | 15 | 0.005 | 14 | 0.005 | 10 |
| 0.003 | 10 | 0.003 | 11 | 0.003 | 9 | 0.003 | 8 | 0.003 | 7 |
| 0.0009 | 0 | 0.0012 | 0 | 0.0012 | 0 | 0.0012 | 0 | 0.0012 | 0 |

Table 2 shows the sediment fingerprint matrix of the sampling point A plotted according to Table 1.

TABLE 2

| Percentage | | | | | | | | |
|---|---|---|---|---|---|---|---|---|
| 86%~100% | 4 | 2 | 0 | 0 | 0 | 0 | 0 | 1 |
| 71%~85% | 0 | 2 | 2 | 0 | 0 | 0 | 0 | 0 |
| 56%~70% | 0 | 1 | 3 | 2 | 0 | 0 | 0 | 0 |
| 41%~55% | 0 | 0 | 0 | 1 | 1 | 0 | 0 | 0 |
| 26%~40% | 0 | 0 | 0 | 2 | 2 | 0 | 0 | 0 |
| 11%~25% | 0 | 0 | 0 | 0 | 2 | 4 | 1 | 0 |
| 1%~10% | 0 | 0 | 0 | 0 | 0 | 1 | 4 | 0 |
| 0 | 1 | 0 | 0 | 0 | 0 | 0 | 0 | 4 |
| Grain size | 0.1 | 0.05 | 0.02 | 0.015 | 0.007 | 0.005 | 0.003 | 0.001 |

Table 3 shows various grain size intervals on five sediment grain size distribution curves of the sampling point B and its four additional testing points as well as the corresponding mass percentages.

TABLE 3

| Grain size distribution curve 1 | | Grain size distribution curve 2 | | Grain size distribution curve 3 | | Grain size distribution curve 4 | | Grain size distribution curve 5 | |
|---|---|---|---|---|---|---|---|---|---|
| Grain size | Percentage | Grain size | Percentage | Grain size | Percentage | Grain size | Percentage | Grain size | Percentage |
| 0.09 | 100 | 0.08 | 100 | 0.075 | 100 | 0.085 | 100 | 0.095 | 100 |
| 0.05 | 95 | 0.05 | 85 | 0.05 | 80 | 0.005 | 83 | 0.005 | 90 |
| 0.02 | 70 | 0.02 | 60 | 0.02 | 65 | 0.02 | 55 | 0.002 | 80 |
| 0.015 | 55 | 0.015 | 30 | 0.015 | 60 | 0.015 | 50 | 0.015 | 38 |
| 0.007 | 32 | 0.007 | 20 | 0.007 | 35 | 0.007 | 24 | 0.007 | 25 |
| 0.005 | 21 | 0.005 | 16 | 0.005 | 10 | 0.005 | 9 | 0.005 | 13 |
| 0.003 | 15 | 0.003 | 11 | 0.003 | 9 | 0.003 | 8 | 0.003 | 7 |
| 0.001 | 0 | 0.0012 | 0 | 0.0015 | 0 | 0.0018 | 0 | 0.0002 | 0 |

Table 4 shows the sediment fingerprint matrix of the sampling point B plotted according to Table 3.

TABLE 4

| Percentage | | | | | | | | |
|---|---|---|---|---|---|---|---|---|
| 86%~100% | 5 | 2 | 0 | 0 | 0 | 0 | 0 | 0 |
| 71%~85% | 0 | 3 | 1 | 0 | 0 | 0 | 0 | 0 |
| 56%~70% | 0 | 0 | 3 | 2 | 0 | 0 | 0 | 0 |
| 41%~55% | 0 | 0 | 1 | 1 | 0 | 0 | 0 | 0 |
| 26%~40% | 0 | 0 | 0 | 2 | 3 | 0 | 0 | 0 |
| 11%~25% | 0 | 0 | 0 | 0 | 2 | 3 | 2 | 0 |
| 1%~10% | 0 | 0 | 0 | 0 | 0 | 2 | 3 | 0 |
| 0 | 0 | 0 | 0 | 0 | 0 | 0 | 0 | 5 |
| Grain size | 0.1 | 0.05 | 0.02 | 0.015 | 0.007 | 0.005 | 0.003 | 0.001 |

In Table 2 and Table 4, the first column represents the maximum grain size, and the last column represents the minimum grain size. Usually, the data in the first column and the last column will not be used for fingerprint comparison. The first column in Table 2 indicates that the grain size of sediment collected from four points is less than 0.1 mm, and the grain size of sediment collected from one point is greater than 0.1 mm. The last column indicates that the grain size of sediment collected from one point is less than 0.001 mm, and the grain size of sediment collected from four points is greater than 0.001 mm.

According to Tables 1 and 2, the fourth column in Table 2 means that the sediment with a mass percentage between 55% to 70% ((55%, 70%]) at two points has a grain size of less than 0.015 mm, the sediment with a mass percentage between 40% to 55% ((40%, 55%]) at one point has a grain size of less than 0.015 mm, and the sediment with a mass percentage between 25% to 40% ((25%, 40%]) at two points has a grain size of less than 0.015 mm.

S400: Comparing the pattern of the sediment fingerprint matrix of the sampling point A with that of the sediment fingerprint matrix of the sampling point B. The fingerprint code of the fourth column of the sampling point A is 00212000, and the fingerprint code of the fourth column of the sampling point B is also 00212000, therefore, the patterns of the sampling point A and the sampling point B are similar, that is, the sediment from the sampling point A and the sediment from the sampling point B have the same source.

Based on the fluvial dynamics and sediment transport dynamics, the general movement direction of sediment at different locations can be determined, and it can be concluded that the source of B is A.

Compared with the prior art, the present disclosure has at least the following beneficial effects:

the present disclosure accurately measures the grain size distribution of sediment and the corresponding mass percentages to form accurate sediment grain size distribution curves of the sampling points and their additional testing points. The sediment fingerprint matrix is provided to accurately show the variation of sediment characteristics in different grain size intervals. The sediment characteristics in the corresponding grain size intervals of the sediment fingerprint matrices from different positions can be compared separately, i.e., the patterns of the grain size intervals of the sediment fingerprint matrices from different positions can be compared. A good match of the patterns indicates that the sediments from different positions have the same source.

The above description only provides preferred embodiments of the present disclosure. It should be noted that, for those skilled in the art, various modifications and substitutions can be made without departing from the technical principles of the present disclosure, and should be considered still within the protection scope of the present disclosure.

The invention claimed is:

1. A method for tracing a sediment source, comprising:

S100: sampling at sampling points and a plurality of additional testing points around each sampling point;

wherein the sampling points comprise a first sampling point and a second sampling point;

S200: measuring sediment grain size distribution and corresponding mass percentages to plot sediment grain size distribution curves of each sampling point and its additional testing points;

S300: plotting a sediment fingerprint matrix of each sampling point;

wherein a horizontal axis of the sediment fingerprint matrix represents grain size, a vertical axis of the sediment fingerprint matrix represents mass percentage, and elements of the sediment fingerprint matrix are the number of the sediment grain size distribution curves;

S400: comparing patterns of the sediment fingerprint matrix of the first sampling point with patterns of the sediment fingerprint matrix of the second sampling point, and determining whether sediment at the first sampling point and that at the second sampling point have the same source, wherein the patterns refer to columns of the sediment fingerprint matrix of each sampling point.

2. The method according to claim 1, wherein a ratio of the number of the sampling points to the number of additional testing points of each sampling point is 1:4, wherein four additional testing points are evenly distributed around each sampling point in a circular pattern.

3. The method according to claim 2, wherein the four additional testing points are respectively located upstream, downstream, and on left and right sides of each sampling point.

4. The method according to claim 1, wherein a distance between each additional testing point and the corresponding sampling point of each additional testing point is in a range of 50 cm to 100 cm.

\* \* \* \* \*